United States Patent
Moser et al.

(10) Patent No.: US 8,886,388 B2
(45) Date of Patent: Nov. 11, 2014

(54) EMBEDDED DAMAGE DETECTION SYSTEM FOR COMPOSITE MATERIALS OF AN AIRCRAFT

(75) Inventors: Matthew A. Moser, Marysville, WA (US); Jeffrey L. Duce, Milton, WA (US); Gregory J. Clark, Seattle, WA (US); John L. Vian, Renton, WA (US); Joseph A. Marshall, Kent, WA (US); Clete M. Boldrin, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 1090 days.

(21) Appl. No.: 12/494,182

(22) Filed: Jun. 29, 2009

(65) Prior Publication Data
US 2012/0197482 A1    Aug. 2, 2012

(51) Int. Cl.
*G01M 5/00* (2006.01)
*G01N 27/20* (2006.01)
*B64C 3/24* (2006.01)

(52) U.S. Cl.
CPC ............. *G01N 27/205* (2013.01); *B64C 3/24* (2013.01); *G01M 5/0033* (2013.01); *G01M 5/0083* (2013.01)
USPC .......... 701/29; 701/29.1; 701/29.6; 701/31.9; 701/34.2

(58) Field of Classification Search
USPC ........ 701/1–3, 14, 29–35; 340/945–983, 500; 73/570, 579, 583, 802
See application file for complete search history.

(56) References Cited

U.S. PATENT DOCUMENTS

| | | | | |
|---|---|---|---|---|
| 3,910,105 A * | 10/1975 | Hoffstedt | ....................... | 73/800 |
| 4,106,332 A * | 8/1978 | McKeown | ..................... | 73/104 |
| 4,629,318 A * | 12/1986 | Malek et al. | ............... | 356/237.1 |
| 4,836,030 A * | 6/1989 | Martin | ........................ | 73/800 |
| 5,142,141 A * | 8/1992 | Talat et al. | ............... | 250/227.15 |
| 5,195,046 A * | 3/1993 | Gerardi et al. | ................ | 702/35 |
| 5,600,133 A * | 2/1997 | Spillman, Jr. | ............ | 250/227.14 |
| 5,816,530 A * | 10/1998 | Grube | .......................... | 244/1 R |
| 5,969,260 A * | 10/1999 | Belk et al. | ........................ | 73/773 |
| 6,006,163 A * | 12/1999 | Lichtenwalner et al. | ....... | 702/36 |
| 6,370,964 B1 * | 4/2002 | Chang et al. | ............ | 73/862.046 |
| 6,486,465 B1 * | 11/2002 | Hein | ........................ | 250/227.14 |
| 6,662,088 B1 * | 12/2003 | Hopple et al. | ............... | 701/301 |
| 6,973,838 B2 * | 12/2005 | Denis | ............................. | 73/799 |
| 6,986,287 B1 * | 1/2006 | Dorfman | ........................ | 73/776 |
| 7,033,667 B2 | 4/2006 | Voss-Kehl et al. | | |
| 7,050,894 B2 * | 5/2006 | Halm et al. | .................. | 701/29.4 |
| 7,080,555 B2 * | 7/2006 | Austin et al. | .................... | 73/587 |

(Continued)

FOREIGN PATENT DOCUMENTS

| | | |
|---|---|---|
| DE | 3622656 | 10/1987 |
| EP | 2103517 | 9/2009 |
| GB | 2405934 | 3/2005 |

OTHER PUBLICATIONS

European Patent Office (International Searching Authority), International Search Report and Written Opinion for PCT/US2010/040053; Oct. 4, 2010.

*Primary Examiner* — Jonathan M Dager
(74) *Attorney, Agent, or Firm* — Klintworth & Rozenblat IP LLC (57) ABSTRACT

A damage-detection apparatus for an aircraft may include a composite structure comprising embedded conductive traces. The embedded conductive traces may be for transmitting a damage-detection signal to indicate if the composite structure has been damaged.

14 Claims, 9 Drawing Sheets

(56) References Cited

U.S. PATENT DOCUMENTS

| | | | |
|---|---|---|---|
| 7,106,215 B2* | 9/2006 | Marishak, Jr. | 340/945 |
| 7,267,008 B2* | 9/2007 | Gordon et al. | 73/587 |
| 7,430,911 B2* | 10/2008 | Qing et al. | 73/587 |
| 7,473,077 B2* | 1/2009 | Gaffiero et al. | 416/61 |
| 7,558,701 B2* | 7/2009 | Andarawis et al. | 702/183 |
| 7,883,050 B2* | 2/2011 | Dufresne et al. | 244/1 A |
| 7,938,012 B2* | 5/2011 | Lv et al. | 73/776 |
| 7,950,289 B2* | 5/2011 | Foote | 73/786 |
| 8,013,600 B1* | 9/2011 | Yepez et al. | 324/240 |
| 2004/0036477 A1* | 2/2004 | Schievelbusch et al. | 324/522 |
| 2005/0284232 A1* | 12/2005 | Rice | 73/762 |
| 2006/0079747 A1* | 4/2006 | Beard et al. | 600/407 |
| 2008/0289426 A1* | 11/2008 | Kearns et al. | 73/632 |
| 2009/0020212 A1* | 1/2009 | Cacace | 156/64 |
| 2009/0259411 A1* | 10/2009 | Loomis et al. | 702/35 |
| 2010/0312420 A1* | 12/2010 | Sham et al. | 701/3 |
| 2011/0219878 A1* | 9/2011 | El-Bakry et al. | 73/583 |
| 2011/0222225 A1* | 9/2011 | Kessler et al. | 361/679.02 |
| 2013/0044155 A1* | 2/2013 | Duce et al. | 347/19 |

* cited by examiner

EMBEDDED DAMAGE DETECTION SYSTEM FOR COMPOSITE MATERIALS OF AN AIRCRAFT

FIELD OF THE INVENTION

The disclosure relates to damage-detection apparatus for an aircraft and to methods for detecting damage in an aircraft.

BACKGROUND OF THE DISCLOSURE

Composite aircraft are being built to decrease weight, decrease fuel consumption, increase speed, and/or decrease cost. These aircraft currently do not have apparatus and/or methods for monitoring damage of the composite parts, such as aircraft flaps or other parts of the aircraft. It would be beneficial to be able to monitor the condition of one or more composite parts of the aircraft for damage. In such manner, corrective measures may be taken in the event that one or more composite parts are damaged.

An apparatus and/or method is needed which may monitor the condition of one or more composite parts of an aircraft for damage.

SUMMARY OF THE DISCLOSURE

In one embodiment, a damage-detection apparatus for an aircraft is disclosed. The damage-detection apparatus may comprise a composite structure comprising embedded conductive traces. The embedded conductive traces may be for transmitting a damage-detection signal to indicate if the composite structure has been damaged.

In another embodiment, an aircraft is disclosed. The aircraft may comprise a composite structure comprising embedded conductive traces. The aircraft may further comprise at least one of a transponder, a transmitter, and a receiver for transmitting and receiving a damage-detection signal through the embedded conductive traces. If the composite structure is damaged to affect the embedded conductive traces, the damage-detection signal may be at least one of changed and interrupted to indicate that the composite structure has been damaged.

In yet another embodiment, a method of detecting damage in an aircraft is disclosed. In one step, a damage-detection signal may be transmitted through embedded conductive traces of a composite structure of the aircraft. In another step, the damage-detection signal may be monitored to determine if the damage-detection signal is at least one of changed and interrupted to indicate that the composite structure has been damaged.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. Details of the electronic circuitry known to those of ordinary skill in the art have not been included in the description to avoid unnecessarily obscuring the disclosure. Those of ordinary skill in the art will know how to configure the disclosure without these known details regarding the electronic circuitry.

Figure 1:
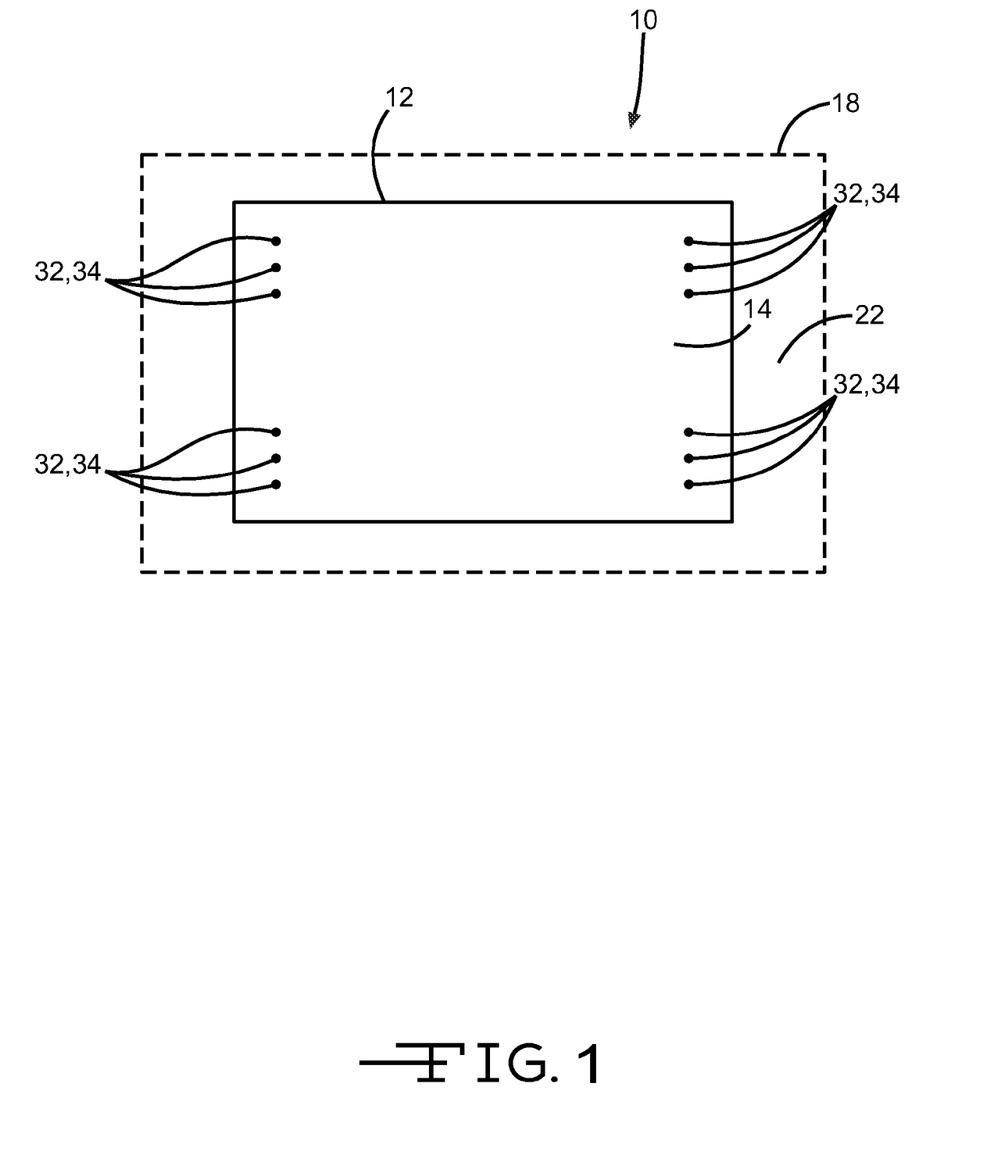
FIG. 1 illustrates a top view of one embodiment of a damage-detection apparatus.
Figure 2:
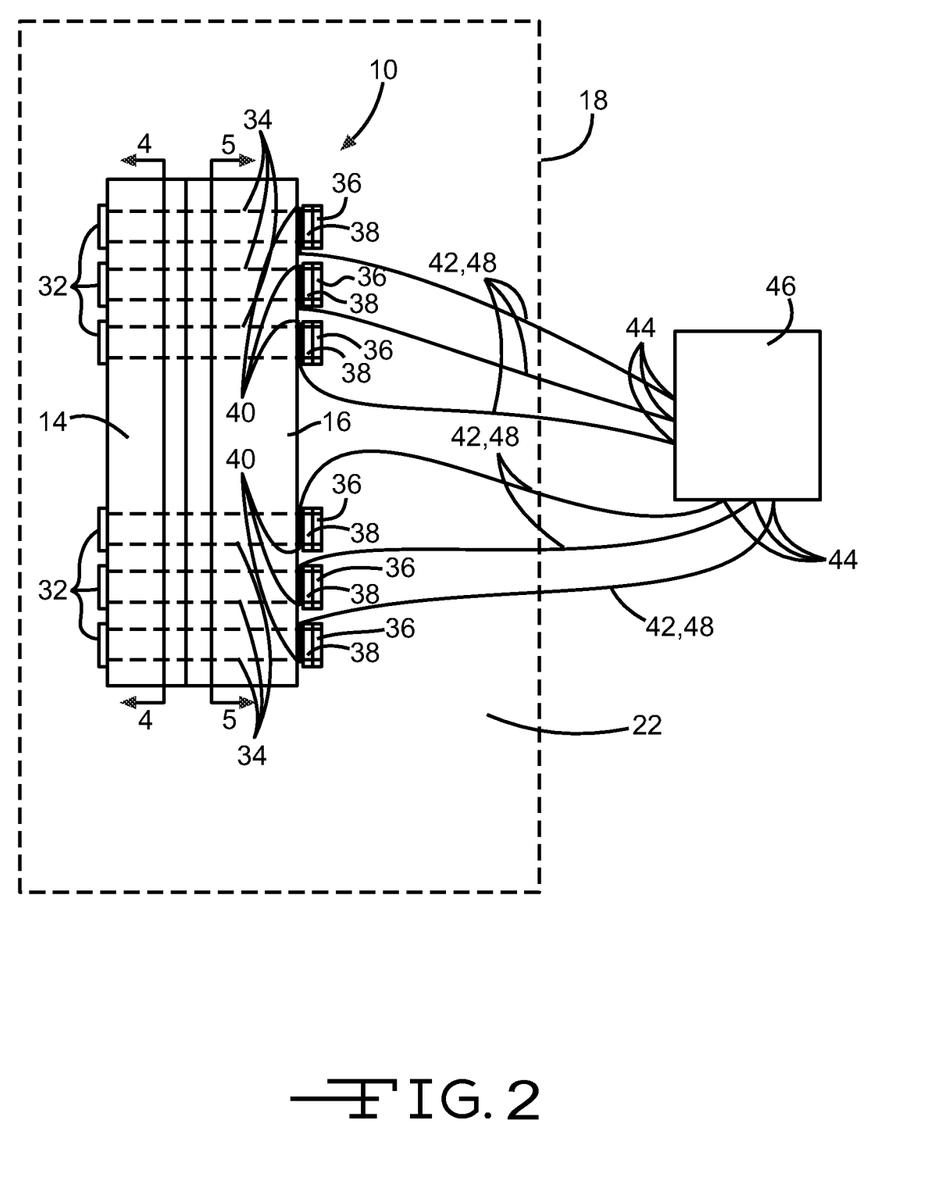
FIG. 2 illustrates a side view of the damage-detection apparatus of FIG. 1.
Figure 3:
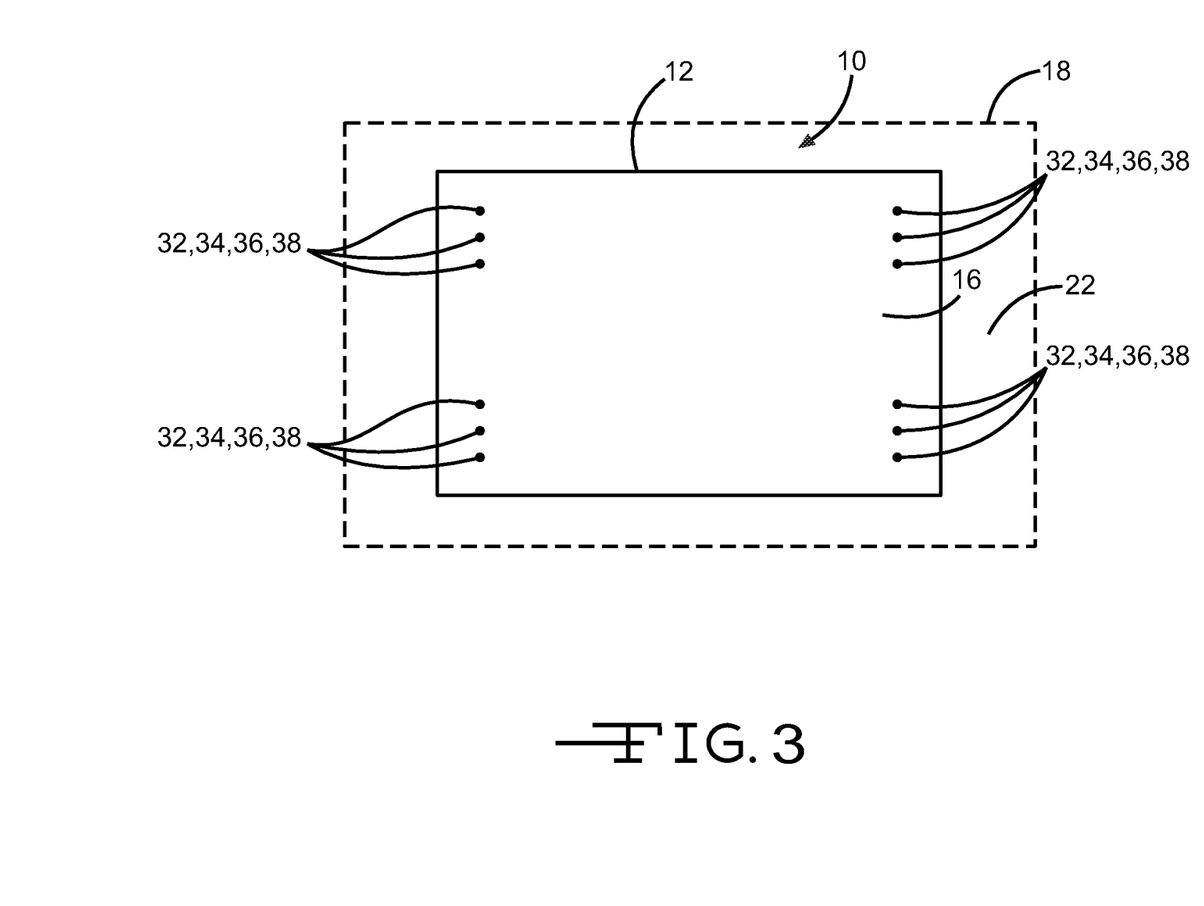
FIG. 3 illustrates a bottom view of the damage-detection apparatus of FIG. 1.
Figure 4:
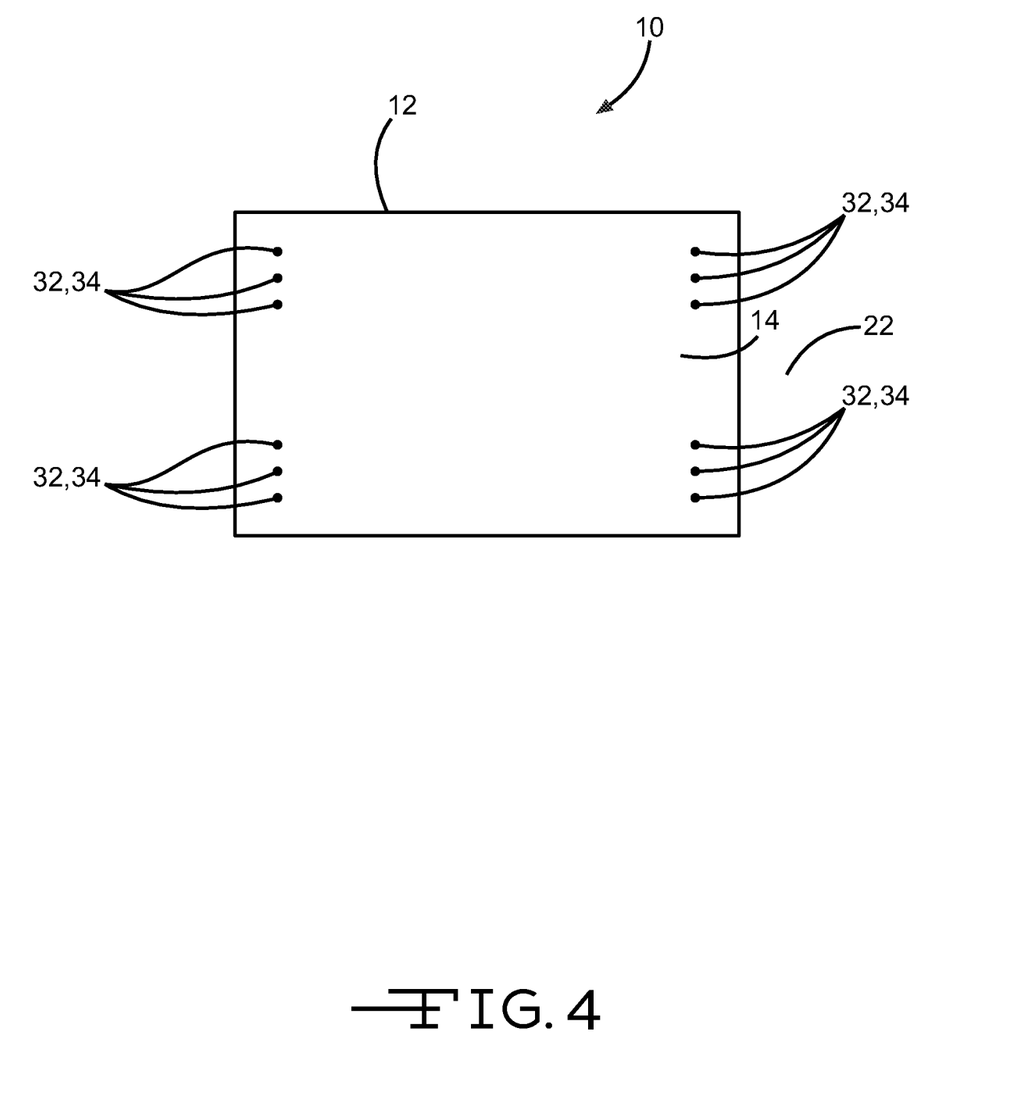
FIG. 4 illustrates a cross-sectional view through line 4-4 of the damage-detection apparatus of FIG. 2.

FIGS. 1-5 illustrate respectively a top view, a side view, a bottom view, and cross-sectional views, through lines 4-4 and 5-5 of FIG. 2, of one embodiment of a damage-detection apparatus 10. The damage-detection apparatus 10 may comprise an aircraft part, such as but not limited to an aircraft flap. As shown in FIGS. 1-5, the damage-detection apparatus 10 may comprise a composite structure 12. As shown in FIG. 2, the composite structure 12 may comprise a first panel 14 adhered to a second panel 16. The first panel 14 may have been adhered to the second panel 16 using an autoclave 18. The first panel 14 may comprise a solid, composite panel. The first panel 14 may be made of Fiberglass or another composite material.

Figure 5:
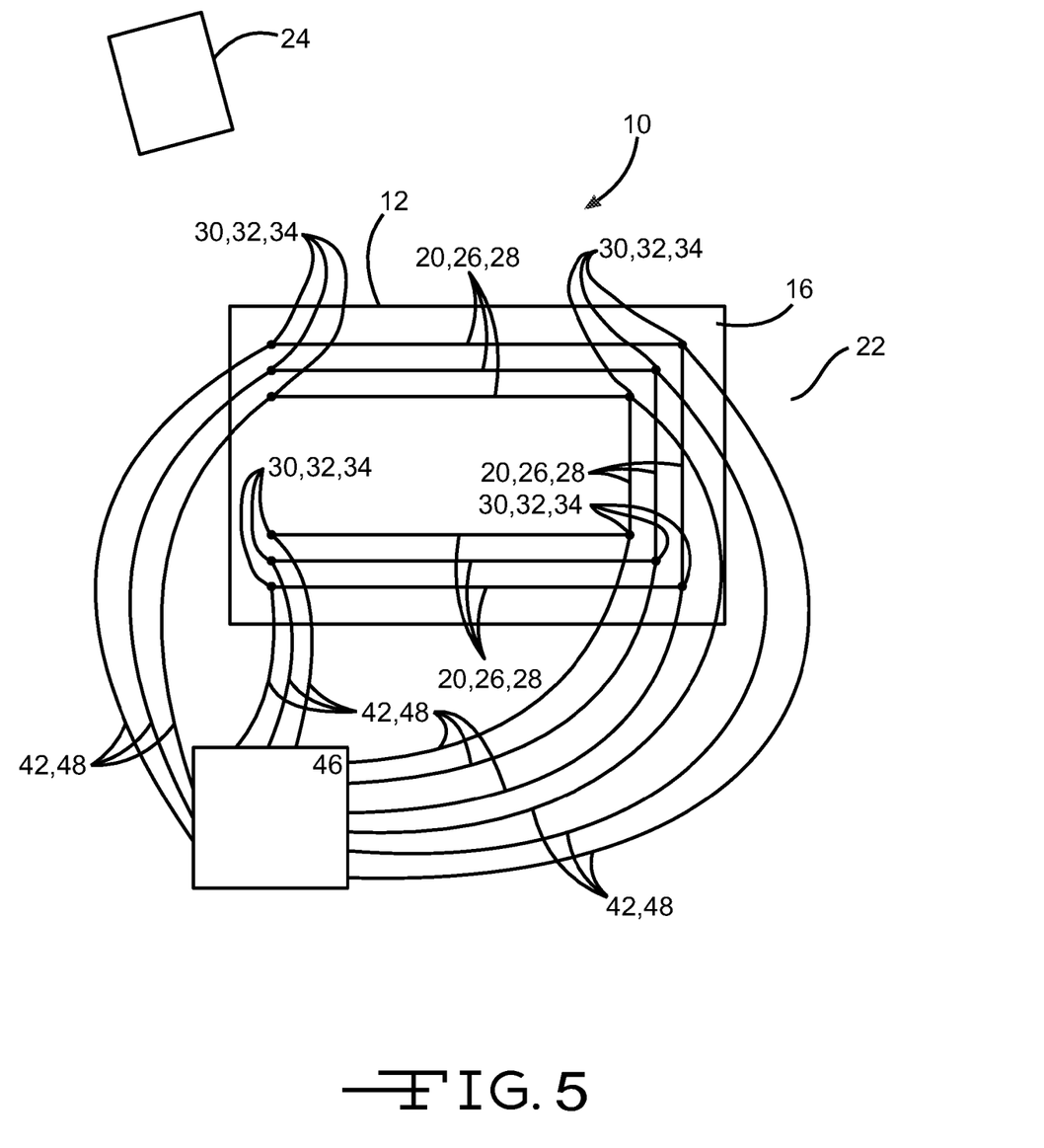
FIG. 5 illustrates a cross-sectional view through line 5-5 of the damage-detection apparatus of FIG. 2 in the scenario where a composite structure of the damage-detection apparatus is undamaged creating a closed-circuit.

As shown in FIG. 5, the second panel 16 may comprise a composite panel having conductive traces 20 embedded within the second panel 16. The second panel 16 may be made of Tedlar or another flexible, thin-film, composite material. The conductive traces 20 may be made of a conductive material such as Copper. The conductive traces 20 may be disposed within the composite structure 12, and may be protected from the environment 22 by the first and second panels 14 and 16. The conductive traces 20 may have been embedded in the second panel 16 using a direct-write device 24 following a direct-write process.

A direct-write process may comprise the additive process of depositing only the required material directly to a substrate. This may differ from standard electronics processing techniques which may require that the substrate be completely covered with the desired material and that the excess material be removed. Direct-write processes may include, but may not be limited to, thermal plasma sprays, nano-particle ink-jets, atomized jetted ink deposition, kinetic metallization, and/or to other types of direct-write processes.

As shown in FIG. 5, the conductive traces 20 may form at least a portion of a loop 26 within the second panel 16 of the damage-detection apparatus 10. The conductive traces 20 may comprise a plurality of conductive lines 28 connected together by distributed conductive pads 30. The second panel 16 may comprise at least twelve conductive pads 30. In other embodiments, varying numbers of conductive pads 30 may be distributed in the second panel 16. As shown in FIG. 2, fasteners 32 may extend through the first and second panels 14 and 16 through holes 34 in the conductive pads 30. The fasteners 32 may comprise threaded screws. The fasteners 32 may be secured to the composite structure 12 using nuts 36 and washers 38. The fasteners 32 may secure ends 40 of conductive wires 42 against the conductive pads 30. At least six of the conductive pads 30 may be connected to the conductive wires 42. In other embodiments, varying numbers of conductive pads 30 may be connected to conductive wires 42. Opposing ends 44 of the conductive wires 42 may be connected to one or more signal devices 46. The one or more signal device 46 may comprise any number of transponders for transmitting and receiving one or more signals, or may comprise any number of separate transmitters working in conjunction with separate receivers to transmit and receive one or more signals. In other embodiments, the one or more signal devices 46 may comprise at least one of a transponder, a transmitter, and a receiver.

As shown in FIGS. 2 and 5, the one or more signal devices 46 may be adapted to transmit and/or receive a damage-detection signal 48 to and/or from the conductive wires 42 through the at least a portion of the loop 26 of the conductive traces 20 using the conductive pads 30 and conductive lines 28. As shown in FIG. 5, when the composite structure 12 of the damage-detection apparatus 10 is undamaged, the loop 26, comprising the conductive traces 20 made up of the conductive pads 30 and the conductive lines 28, may create a closed circuit. The closed circuit may transmit the damage-detection signal 48 from the one or more signal devices 46, through the conductive wires 42, through the loop 26, and may receive the damage-detection signal 48 back at the one or more signal devices 46. The one or more signal devices 46 may continually monitor the damage-detection signal 48 and may determine that the damage-detection signal 48 has not changed, and that therefore the composite structure 12 of the damage-detection apparatus 10 has not been damaged.

Figure 6:
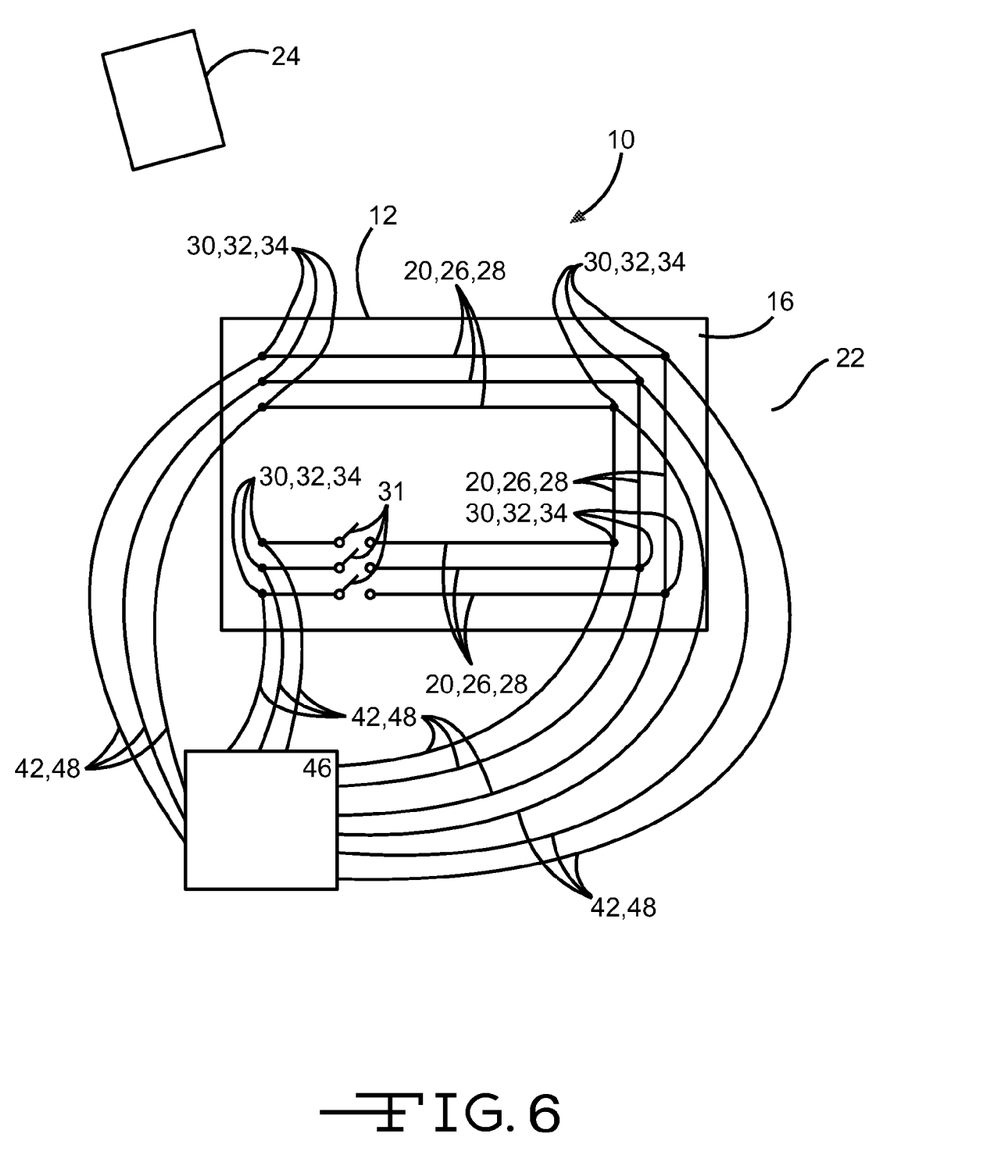
FIG. 6 illustrates the cross-sectional view of the damage-detection apparatus of FIG. 5 in the scenario where the composite structure of the damage-detection apparatus has been damaged creating an open-circuit.

FIG. 6 illustrates the cross-sectional view of the damage-detection apparatus 10 of FIG. 5 in the scenario where the composite structure 12 of the damage-detection apparatus 10 has been damaged creating an open circuit. As shown in FIG. 6, the composite structure 12 of the damage-detection apparatus 10 has been damaged creating a break 31 in the loop 26 of the conductive traces 20 comprising the conductive pads 30 and the conductive lines 28. As a result, because the composite structure 12 of the damage-detection apparatus 10 has been damaged, the loop 26 may now form an open circuit. The damage-detection signal 48 may be transmitted from the one or more signal devices 46 and through the conductive wires 42, but the damage-detection signal 48 may be interrupted at the break 31 in the loop 26 of the conductive traces 20. As a result of the break 31 in the loop 26, the one or more signal devices 46 may not receive the damage-detection signal 48, and/or may receive an altered damage-detection signal 48. This may indicate that the composite structure 12 of the damage-detection apparatus 10 may have been damaged which may be useful information to a pilot, to a maintenance crew, and/or to another type of user. By using distributed conductive pads 30, each individually connected to the one or more signal devices 46, a determination may be made as to a location of the break 31 in the composite structure 12 of the damage-detection apparatus 10 in order to pinpoint the location of the damage.

Figure 7:
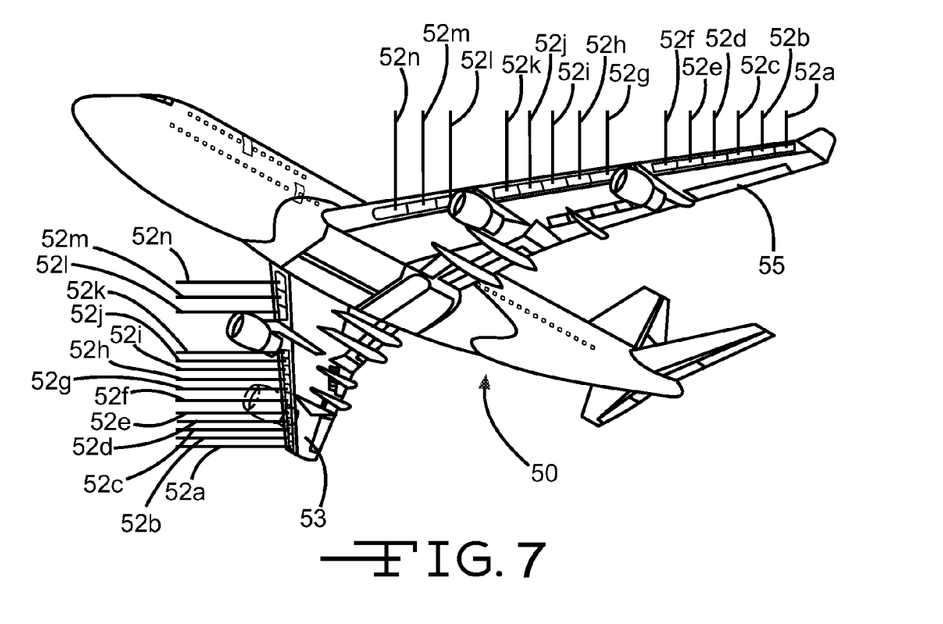
FIG. 7 illustrates a perspective view of one embodiment of an aircraft in which one or more of the damage-detection apparatus of FIG. 1 may be used.

FIG. 7 illustrates a perspective view of one embodiment of an aircraft 50. One or more of the damage-detection apparatus 10 of FIGS. 1-6 may be used in the aircraft 50. The aircraft 50 may comprise a plurality of aircraft flaps 52a-52n on wings 53 and 55. One or more of the aircraft flaps 52a-52n may comprise one or more of the damage-detection apparatus 10 of FIGS. 1-6. As shown in FIG. 2, each damage-detection apparatus 10 may be connected to one or more signal devices 46 of the aircraft 50 (shown in FIG. 7) using conductive wires 42. In such manner, the aircraft 50 may detect when one or more of the aircraft flaps 52a-52n have been damaged during flight, such as if a hole has been formed in one or more of the aircraft flaps 52a-52n, allowing the pilot to take the appropriate measures to accommodate for the damaged flaps 52a-52n.

In one embodiment, each of aircraft flaps 52g-52h of each wing 53 and 55 may comprise the damage-detection apparatus 10 of FIGS. 1-6, allowing the aircraft 50 to monitor damage to any of flaps 52g-52h. In other embodiments, one or more of the other flaps 52a-52f and 52h-52n may comprise the damage-detection apparatus 10 of FIGS. 1-6. In still other embodiments, one or more other internal or external non-flap components of the aircraft 50 may comprise the damage-detection apparatus 10 of FIGS. 1-6.

Figure 8:
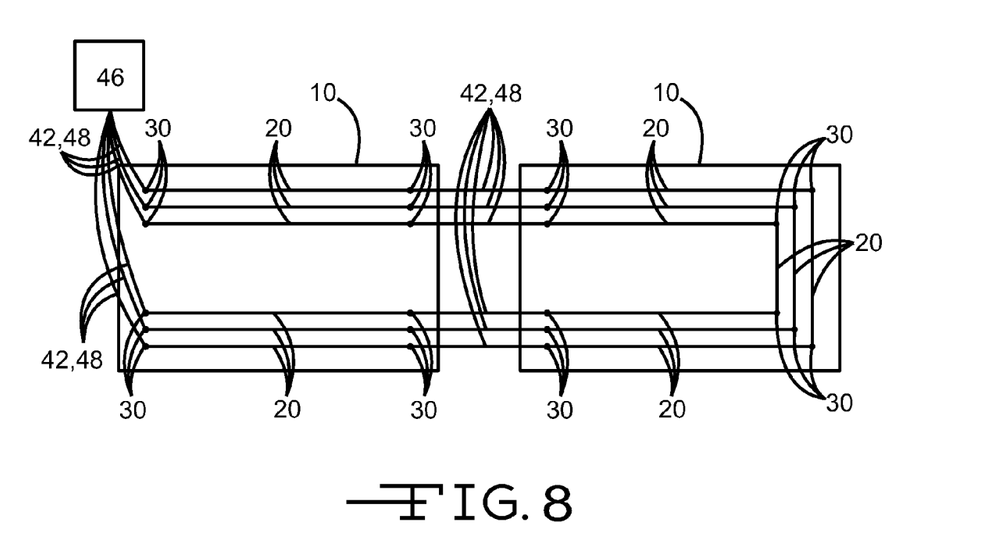
FIG. 8 illustrates a representative cross-section view of one embodiment of a plurality of interlinked damage-detection apparatus which may be used in the aircraft of FIG. 7.

FIG. 8 illustrates a representative cross-section view of another embodiment of a plurality of interlinked damage-detection apparatus 10 which may be used in the aircraft 50 of FIG. 7 for any number of the aircraft flaps 52a-52n. As shown, the plurality of interlinked damage-detection apparatus 10 may be connected together in series by the conductive wires 42 extending between and connecting conductive pads 30 of the conductive traces 20 of each interlinked damage-detection apparatus 10. It is noted that the plurality of interlinked damage-detection apparatus 10 utilize varying shaped conductive traces 20. In other embodiments, any number of interlinked damage-detection apparatus 10, using varying patterns of conductive traces 20, may be connected in series or in parallel.

The conductive wires 42 may run to the one or more signal devices 46 which may be installed in the aircraft 50 of FIG. 7. The one or more signal devices 46 may transmit and receive a damage-detection signal 48 through the circuit loop formed by the conductive wires 42 and the conductive traces 20 of the interlinked damage-detection apparatus 10. If one or more of the damage-detection apparatus 10 is oriented in a wrong position, one or more of the conductive wires 42 may be adapted to break. This may cause the closed circuit to become an open circuit thereby changing, interrupting, and/or stopping the signal 48 received by the one or more signal devices 46. This may signal the pilot that one or more of the damage-detection apparatus 10 is in a wrong position. The pilot may take appropriate measures to accommodate for the one or more out-of-position damage-detection apparatus 10. In other embodiments, the plurality of interlinked damage-detection apparatus 10 may be connected in varying ways.

Figure 9:
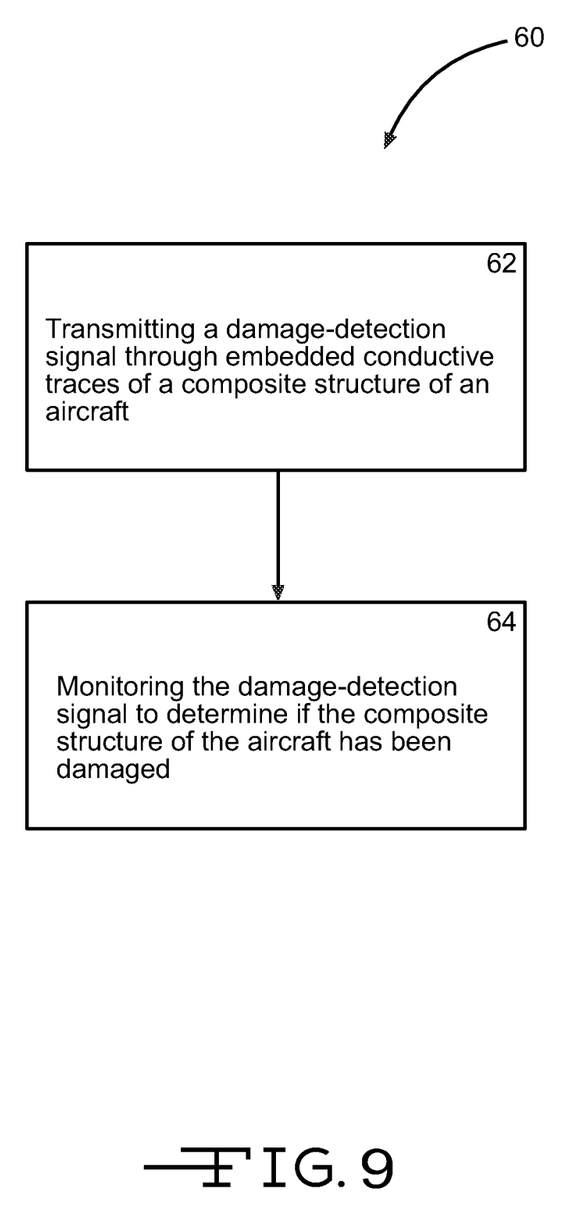
FIG. 9 illustrates a flowchart of one embodiment of a method for detecting damage in an aircraft.

FIG. 9 illustrates a flowchart of one embodiment of a method 60 for detecting damage in an aircraft 50. In step 62, a damage-detection signal 48 may be transmitted through embedded conductive traces 20 of a composite structure 12 of an aircraft 50. The composite structure 12 may comprise one or more aircraft flaps 52a-52n. Any number of the aircraft flaps 52a-52n may have the embedded conductive traces 20. In other embodiments, the composite structure 12 may comprise other components of the aircraft 50. Step 62 may comprise one or more signal devices 46 transmitting the damage-detection signal 48 through conductive wires 42 connected to conductive pads 30 of the embedded conductive traces 20 of the composite structure 12. In one embodiment, conductive wires 42 may extend between the conductive embedded traces 20 of any number of the separate aircraft flaps 52a-52n.

In step 64, the damage-detection signal 48 may be monitored to determine if the damage-detection signal 48 is at least one of changed and interrupted indicating that the composite structure 12 has been damaged. Step 64 may comprise one or more signal devices 46 receiving the damage-detection signal 48 from the conductive pads 30 of the embedded conductive traces 20 through the conductive wires 42. The conductive pads 30 may be distributed in the composite structure 12 to monitor distributed locations of the composite structure 12 for damage. In one embodiment, conductive wires 42 extending between the conductive embedded traces 20 of any number of the separate aircraft flaps 52a-52n may break if at least one of the aircraft flaps 52a-52n is oriented in a wrong position. This may change and/or interrupt the damage-detection signal 48 indicating to the one or more signal devices 46 that one or more of the aircraft flaps 52a-52n is oriented in the wrong position. The pilot of the aircraft 50 may then take appropriate measures to accommodate for the situation. The method 60 may also be used by maintenance crew, and/or by other types of uses to determine when damage has occurred to any type of composite structure 12 of the damage-detection apparatus 10.

Figure 10:
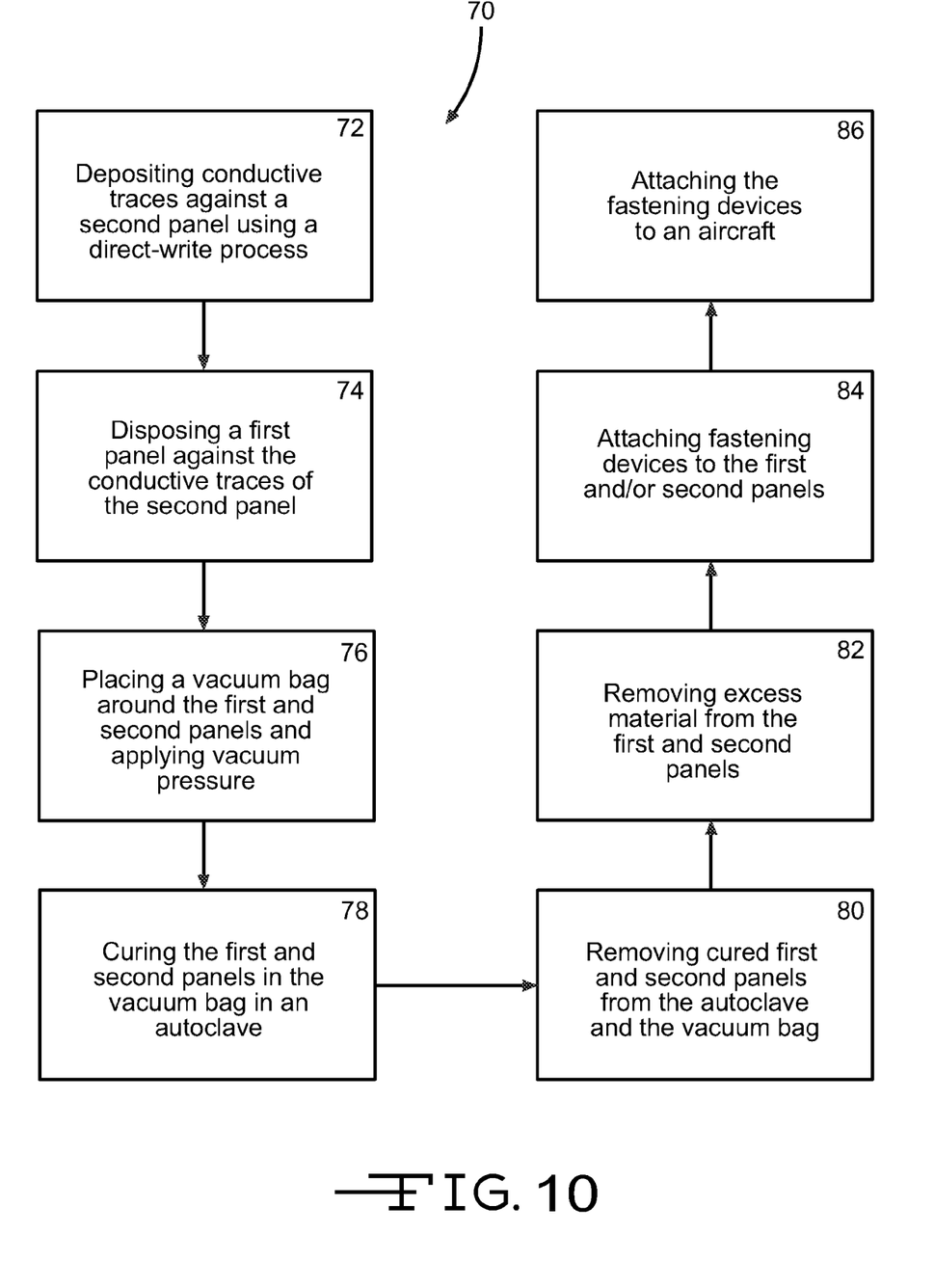
FIG. 10 illustrates a flowchart of one embodiment of a method for manufacturing a damage-detection apparatus.

FIG. 10 illustrates a flowchart of one embodiment of a method 70 for manufacturing a damage-detection apparatus 10. In step 72, conductive traces 20 may be deposited against a surface of a second panel 16 using a direct-write process. In step 74, a surface of a first panel 14 may be disposed against the surface of the second panel 16 having the deposited conductive traces 20 to create a sandwich. In step 76, a vacuum bag may be placed around the sandwich and vacuum pressure may be applied. In step 78, the vacuum bag may be placed in an autoclave and the sandwich may be cured. In step 80, the vacuum bag may be removed from the autoclave and the sandwich may be removed from the vacuum bag. In step 82, excess material may be trimmed from the first and second panels 14 and 16. In step 84, fastening devices, such as brackets, stringers, or other types of fastening devices, may be attached to one or more of the first and second panels 14 and 16. In step 86, the fastening devices may be attached to an aircraft 50.

One or more apparatus and/or methods of the disclosure may allow for the monitoring of damage of composite parts, such as aircraft flaps or other parts of an aircraft. By monitoring these parts, corrective measures may be taken in the event that one or more composite parts are damaged.

It should be understood, of course, that the foregoing relates to exemplary embodiments of the disclosure and that modifications may be made without departing from the spirit and scope of the disclosure as set forth in the following claims.

We claim:

1. A damage-detection apparatus for an aircraft comprising:
a composite structure comprising a panel attached to a polymer film, and conductive traces embedded within the polymer film, the conductive traces configured to transmit a damage-detection signal along the conductive traces to indicate that the composite structure has been damaged when there is a break in the conductive traces, wherein the conductive traces comprise a plurality of conductive lines connected together by fasteners extending into holes disposed within the panel, the polymer film, and conductive pads, the conductive pads being disposed against the polymer film.

2. The damage-detection apparatus of claim 1 wherein the panel is made of a fiber reinforced polymer.

3. The damage-detection apparatus of claim 1 wherein the composite structure comprises an aircraft flap.

4. The damage-detection apparatus of claim 1 wherein the polymer film comprises a polyvinyl fluoride film.

5. The damage-detection apparatus of claim 2 wherein the panel is made of fiberglass.

6. The damage-detection apparatus of claim 1 wherein the conductive traces form at least a portion of a loop within the composite structure.

7. An aircraft comprising:
a composite structure comprising a panel attached to a polymer film, and conductive traces embedded within the polymer film; and
a transponder, or a transmitter and a receiver, configured to transmit and receive a damage-detection signal along the embedded conductive traces to indicate that the composite structure has been damaged when there is a break in the conductive traces;
wherein the conductive traces comprise a plurality of conductive lines connected together by fasteners extending into holes disposed within the panel, the polymer film, and conductive pads, the conductive pads disposed against the polymer film, a plurality of the conductive pads being connected to conductive wires which are connected to the transponder or to the transmitter and the receiver.

8. The aircraft of claim 7 wherein the composite structure comprises at least one aircraft flap.

9. The aircraft of claim 7 wherein the panel is made of a fiber reinforced polymer.

10. The aircraft of claim 7 wherein the polymer film comprises a polyvinyl fluoride film.

11. The aircraft of claim 7 wherein the conductive traces form at least a portion of a loop within the composite structure.

12. The aircraft of claim 7 wherein the conductive traces are distributed in the composite structure and configured to provide a location of damage in the composite structure.

13. The aircraft of claim 9 wherein the panel is made of fiberglass.

14. The aircraft of claim 7 wherein the composite structure comprises a plurality of aircraft flaps, each of the aircraft flaps having the conductive embedded traces, wherein the conductive wires extend between the conductive embedded traces of separate aircraft flaps, the conductive wires configured to break when at least one of the aircraft flaps is oriented in a wrong position.

* * * * *